(12) United States Patent
Rajadas et al.

(10) Patent No.: US 9,283,289 B2
(45) Date of Patent: Mar. 15, 2016

(54) SELF-QUENCHING ACTIVATABLE COX-2-SPECIFIC MULTI-MODAL MOLECULAR PROBES FOR DIAGNOSIS OF CANCERS, INFLAMMATION, AND IMMUNE SYSTEM DISORDERS

(71) Applicant: The Board of Trustees of the Leland Stanford Junior University, Palo Alto, CA (US)

(72) Inventors: Jayakumar Rajadas, Cupertino, CA (US); Emilio Gonzalez, Madrid (ES); Hyejun Ra, Sunnyvale, CA (US); Irfan Ali-Khan, Saratoga, CA (US); Christopher Contag, San Jose, CA (US)

(73) Assignee: THE BOARD OF TRUSTEES OF THE LELAND STANFORD JUNIO CA (US)

( * ) Notice: Subject to any disclaimer, the term of this patent is extended or adjusted under 35 U.S.C. 154(b) by 140 days.

(21) Appl. No.: 13/932,085

(22) Filed: Jul. 1, 2013

(65) Prior Publication Data
US 2014/0004050 A1    Jan. 2, 2014

Related U.S. Application Data

(60) Provisional application No. 61/667,076, filed on Jul. 2, 2012.

(51) Int. Cl.
| | |
|---|---|
| *A61B 10/00* | (2006.01) |
| *A61B 5/00* | (2006.01) |
| *A61B 8/00* | (2006.01) |
| *A61K 49/00* | (2006.01) |
| *G01N 21/64* | (2006.01) |
| *A61K 31/405* | (2006.01) |
| *A61K 31/415* | (2006.01) |
| *A61K 31/4375* | (2006.01) |

(52) U.S. Cl.
CPC ............ *A61K 49/006* (2013.01); *A61K 31/405* (2013.01); *A61K 31/415* (2013.01); *A61K 31/4375* (2013.01); *A61K 49/0041* (2013.01); *A61K 49/0052* (2013.01); *G01N 21/6428* (2013.01); *G01N 21/6486* (2013.01); *G01N 21/6456* (2013.01); *G01N 2021/6432* (2013.01)

(58) Field of Classification Search
CPC .............. A61K 49/00; A61K 49/0041; A61K 49/0052; A61K 49/0032; A61K 49/0056; A61K 49/0057; A61K 49/0021; A61K 49/0033; A61K 31/00; A61K 31/405; A61K 31/415; A61K 31/4375; A61K 49/006; G01N 21/6456; G01N 21/6428; G01N 2021/6432; G01N 21/6486
USPC ............. 424/1.11, 1.65, 1.69, 9.1, 9.6; 514/1, 514/1.1, 19.2
See application file for complete search history.

(56) References Cited

U.S. PATENT DOCUMENTS

2007/0041904 A1 *  2/2007  Jiang et al. ................... 424/1.69

OTHER PUBLICATIONS

Uddin et al, Cancer Res., 2010, vol. 70, No. 9, pp. 3618-3627.*
Zheng et al, Organic Letters, 2001, vol. 3, No. 21, pp. 3277-3280.*
International Search Report and Written Opinion dated Sep. 6, 2013.
Wysong, et al., "Non-Invasive of NMSC Using a Targeted Fluorocoxib Probe: Potential for Early Detection, Guided Biopsies, and Improved Margin Control," American College of Mohs Surgery, 44th Annual Meeting, Chicago, IL, May 2012, pp. 51-79.
Ogawa, et al., "Activatable Optical Imaging Probes with Various Fluorophore-Quencher Combinations," Proceeding of SPIE, 2009, vol. 7190, pp. 71900A,1-71900Z.8.
Zheng, et al., A New Fluroescent Chemosensor for Copper Ions Based on Tripeptide Glycyl-histidyl-lysine (GHK), Organic Letters, 2001, vol. 3, No. 21, pp. 3277-3280.
Kobayashi, et al., "Target-Cancer-Cell-Specific Activatable Fluorescence Imaging Probes: Rational Design and In Vivo Applications," Accounts of Chemical Research, 2011, vol. 44, No. 2, pp. 83-90.
De Leeuw, et al., "Fluorescence Detection and Diagnosis of Non-Melanoma Skin Cancer at an Early Stage," Lasers in Surgery and Medicine, 2009, vol. 41, No. 2, pp. 96-103.
Tiwari, et al., "Drug Delivery Systems: An Updated Review" International Journal of Pharmaceutical Investigation, Jan. 2012, vol. 2, No. 1, pp. 2-11.
Cibiel, et al., "In Vivo Uses of Aptamers Selected Against Cell Surface Biomarkers for Therapy and Molecular Imaging," Biochimie, Feb. 23, 2012, vol. 94, pp. 1595-1606.
Rizzo M.T., Cyclooxygenase-2 in oncogenesis. Clinica Chimica Acta, 2011 412: 671-687.
An et al., Cyclooxygenase-2 expression in murine and human nonmelanoma skin cancers: Implications for therapeutic approaches. Photochemistry and Photobiology, 2002 76: 73-80.
Kujubu et al., TIS10, a phorbol ester tumor promoter-inducible mRNA from Swiss 3T3 cells, encodes a novel prostaglandin synthase/cyclooxygenase homologue. Journal of Biological Chemistry 1991 266, 12866-12872.
O'Banion et al., cDNA cloning and functional activity of a glucocorticoid-regulated inflammatory cyclooxygenase (1992) Proceedings of the National Academies of Science U.S.A. 1992 89: 4888-4892.
Uddin et al., Selective Visualization of Cyclooxygenase-2 in Inflammation and Cancer by Targeted Fluorescent Imaging Agents Cancer Reseach 2010 70: 3618-3627.

* cited by examiner

*Primary Examiner* — D L Jones
(74) *Attorney, Agent, or Firm* — Thomas|Horstemeyer, LLP

(57) ABSTRACT

Encompassed are pharmaceutically acceptable compositions formulated for the topical or transdermal delivery of probes specific for cyclooxygenase-2 (COX-2) of human and non-human subjects. In particular, an activatable probe comprises a fluorescent moiety comprising a fluorophore attached to a compound having selective affinity for COX-2, and a removable fluorescence quencher linked to the fluorescent moiety by a cleavable linker. Upon delivery to a recipient subject, the activatable probe is localized and concentrated in tissues and cells with elevated levels of COX-2. The linker is cleaved to release the fluorescence quencher. Irradiation by an activating incident illumination results in a detectable fluorescent emission signal

6 Claims, 8 Drawing Sheets

SELF-QUENCHING ACTIVATABLE COX-2-SPECIFIC MULTI-MODAL MOLECULAR PROBES FOR DIAGNOSIS OF CANCERS, INFLAMMATION, AND IMMUNE SYSTEM DISORDERS

CROSS-REFERENCE TO RELATED APPLICATION

This application claims priority to U.S. Provisional Patent Application Ser. No.: 61/667,076 entitled "SELF-QUENCHING ACTIVATABLE COX-2-SPECIFIC MULTI-MODAL MOLECULAR PROBES FOR DIAGNOSIS OF CANCERS, INFLAMMATION, AND IMMUNE SYSTEM DISORDERS" filed on Jul. 2, 2012, which is hereby incorporated by reference in its entirety.

STATEMENT REGARDING FEDERALLY SPONSORED RESEARCH OR DEVELOPMENT

This invention was made with Government support under contract CA136465 awarded by the National Institutes of Health. The Government has certain rights in this invention.

FIELD OF THE DISCLOSURE

The present disclosure relates to pharmaceutical formulations comprising self-quenching fluorescent molecular probes suitable for topical application to detect epithelial cancers.

BACKGROUND

Cyclooxygenase-2 (COX-2) is highly up-regulated in cancer cells (Rizzo M.T (2011) *Clin. Chim. Acta.* 412: 671-687) and has been reported to be one of the best prognostic indicators for some cancers (An et al., (2002) *Photochem. Photobiol.* 76: 73-80). Imaging agents based on the well-characterized COX-2 inhibitors can be used for the early detection of skin cancer and help define tumor margins. It has previously been shown in a genetically engineered mouse model of non-melanoma skin cancer (NMSC) that systemic administration of (1 mg/kg) 5-Rox-D-indomethacin (Fluorocoxib) enabled visualization of small (approximately 100 µm) tumors (FIG. 1, arrows). A continuing problem is the detection of small tumors that are indistinguishable over non-specific background fluorescence.

SUMMARY

The present disclosure encompasses compositions for the fluorescent detection of COX-2 activity in tumor cells in a reduced background fluorescence. Accordingly, one aspect of the disclosure encompasses embodiments of a composition comprising an activatable probe for the detection of a cell or tissue having cyclooxygenase-2 (COX-2) activity, said activatable probe comprising: (i) a fluorescent moiety comprising a compound capable of selectively binding to COX-2 and a first fluorophore attached thereto; and (ii) a fluorescence quencher selected to quench a fluorescent emission from said fluorophore, wherein the fluorescent moiety and the fluorescence quencher are connected by a cleavable linker.

In embodiments of this aspect of the disclosure, the compound capable of selectively binding to COX-2 can be a COX-2 inhibitor.

In embodiments of this aspect of the disclosure, the COX-2 inhibitor can be indomethacin, celecoxib, or a derivative thereof.

In embodiments of this aspect of the disclosure, the fluorescent moiety can be a Fluorocoxib.

In embodiments of this aspect of the disclosure, the fluorescent quencher can be selected from the group consisting of: a peptide, a peptide in association with a metal ion, deferoxamine, D-penicillamine, dimercaptosuccinic acid, and 2,3-dimercapt-propane-sulfonate.

In embodiments of this aspect of the disclosure, the fluorescent quencher can be a second fluorophore that quenches an emission from the first fluorophore when attached to the fluorescent moiety.

In embodiments of this aspect of the disclosure, the cleavable linker can be cleavable by an enzyme, by a change in pH, or by the redox potential of a tumor or cancerous cell.

In embodiments of this aspect of the disclosure, the cleavable linker comprises a cleavable disulfide bond or a peptide bond.

In some embodiments of this aspect of the disclosure, the activatable probe is encapsulated in a liposome. In these embodiments of this aspect of the disclosure, the liposome can further comprise a biocompatible compound for selectively delivering the liposome to an epithelial cell of the intestinal tract of a human or non-human animal subject.

In embodiments of this aspect of the disclosure, the biocompatible compound can be selected from the group consisting of: sulfasalazine, balsalazide, and olsalazine.

In embodiments of this aspect of the disclosure, the activatable probe can consist essentially of Fluorocoxib A conjugated to GHK-$Cu^+$ or Fluorocoxib A conjugated to DFO-$Cu^+$.

In embodiments of this aspect of the disclosure, the composition can further comprise a pharmaceutically acceptable carrier.

Another aspect of the disclosure encompasses embodiments of a method of detecting a COX-2 activity in a human or non-human animal tissue or cell thereof, the method comprising the steps of: (a) administering to a recipient human or non-human animal subject a pharmaceutically acceptable composition comprising an activatable probe comprising: (i) a fluorescent moiety comprising a compound capable of selectively binding to COX-2 and a fluorophore attached thereto; and (ii) a fluorescence quencher selected to quench a fluorescent emission from said fluorophore, wherein the fluorescent moiety and the fluorescence quencher are connected by a cleavable linker; and a pharmaceutically acceptable carrier, wherein the pharmaceutically acceptable composition can be delivered to the recipient subject by a route that delivers the activatable probe to a tissue suspected of having COX-2 activity; (b) irradiating the recipient tissue or isolated cell with a stimulatory incident energy, whereupon the fluorophore can emit a detectable signal if the fluorescence quencher has been cleaved from the fluorescent molecular probe; and (c) detecting the emitted detectable signal, thereby detecting the presence of COX-2 in the recipient tissue or cell.

In embodiments of this aspect of the disclosure, the pharmaceutically acceptable composition can be formulated for transdermal delivery to the skin or an epithelial surface of the recipient subject, and in step (a) said composition can be administered topically to the skin or an epithelial surface of the recipient subject.

In embodiments of this aspect of the disclosure, the method can further comprise the steps of: (i) obtaining an image of the detectable signal; and (ii) overlaying the image from step (i)

onto an image of the recipient human or non-human animal subject, thereby determining the location of COX-2 in a tissue of said subject.

In embodiments of this aspect of the disclosure, the activatable probe can comprise Fluorocoxib A conjugated to GHK-Cu$^+$ or Fluorocoxib A conjugated to DFO-Cu$^+$.

In embodiments of this aspect of the disclosure, the probe can be encapsulated in a liposome.

BRIEF DESCRIPTION OF THE DRAWINGS

Many aspects of the disclosure can be better understood with reference to the following drawings.

FIG. 1A: Histology and identification of tumor cell; FIG. 1B: from lesion 3 (arrows).

DETAILED DESCRIPTION

Figure 1A:
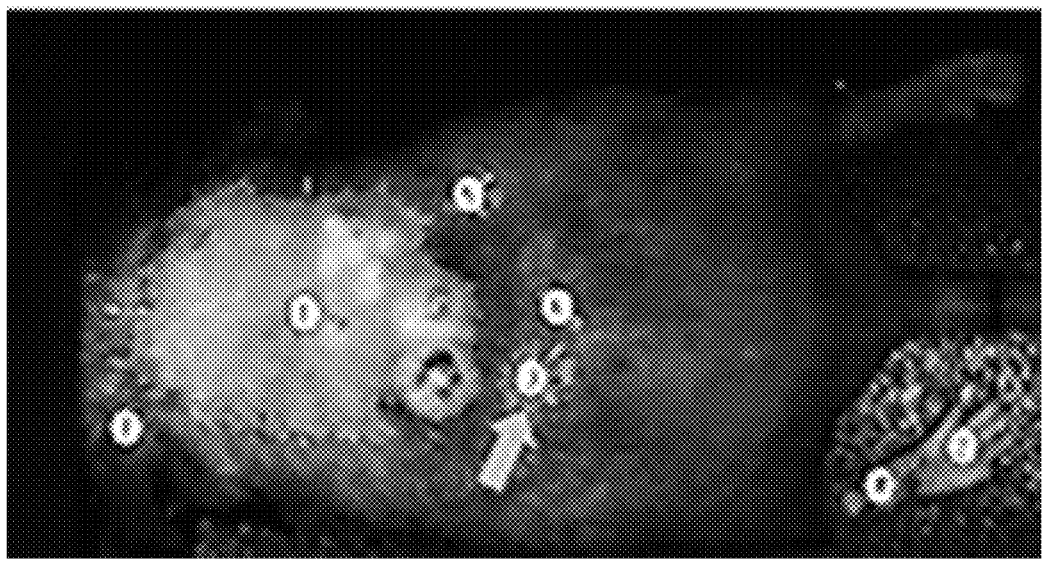
FIGS. 1A and 1B illustrate in vivo detection of Fluorocoxib accumulation in Basal Cell Carcinoma Imaging with CRi Maestro.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Definitions

In describing and claiming the disclosed subject matter, the following terminology will be used in accordance with the definitions set forth below.

The term "administration" as used herein refers to introducing an embodiment of the present disclosure into a recipient human or non-human subject. Administration can include routes such as, but not limited to, topical, subcutaneous, intraperitoneal, intraarterial, inhalation, vaginal, rectal, nasal, or any route that delivers compositions of the disclosure to epithelial tissues. For contacting a skin surface for the detection of such as a melanoma or non-melanoma skin cancer, the compositions of the disclosure may be administered topically to the surface of the skin.

The term "cell or population of cells" as used herein refers to an isolated cell or plurality of cells excised from a tissue or grown in vitro by tissue culture techniques. In the alternative, a population of cells may also be a plurality of cells in vivo in a tissue of an animal or human host. Accordingly, it is intended that the compositions of the disclosure and their methods of use may be applied for the detection of any cell, isolated or in situ in a human or non-human animal.

The term "delivering" as used herein refers to delivering a composition such as a composition according to the present disclosure with or without a pharmaceutically or physiologically acceptable carrier to an isolated or cultured cell or population of cells, or administering the probe in a suitable pharmaceutically acceptable carrier to a human or non-human animal subject. Thereupon, it may be systemically delivered to the target and other tissues of the host, or delivered to a localized target area of the host. Administration may be, but is not limited to, intravenous delivery, intraperitoneal delivery, intramuscularly, subcutaneously or by any other method known in the art. One method is to deliver the composition directly into a blood vessel leading immediately into a target organ or tissue such as an organ having a tumor cell mass, thereby reducing dilution of the probe in the general circulatory system.

The term "activatable probe" as used herein refers to a composition that comprises a ligand that selectively binds to a COX-2 molecule, a fluorophore conjugated to said ligand and which will emit a fluorescent light when illuminated with an incident energy, and a fluorescence quencher attached to the ligand and/or the fluorophore by a cleavable linker. Before administering to a human or non-human animal subject, the quencher will suppress a detectable emission from the fluorophore, for example by adsorbing a fluorescence emission from the fluorophore but not subsequently re-emitting the energy at the same or a different wavelength. Upon delivery or concentration of the probe in a cellular or tissue environment that includes such as an enzyme or physiological condition capable of cleaving the linker, the linker is cleaved to release the quencher from the probe composition. Activation of the probe results from the separation of the quencher from the vicinity of the fluorophore allowing the emission from the fluorophore to be detected.

The term "cyclooxygenase-2" as used herein refers to an enzyme that can catalyze the formation of prostaglandin ("PG")-$H_2$ from arachidonic acid (AA). PG-$H_2$ is further metabolized to physiologically active PGs (e.g., PG-$D_2$, PG-$E_2$ and PG-$F_2\alpha$.), prostacyclin (PG-$I_2\alpha$) and thromboxanes. Specific PGs have diverse, often antagonistic effects on different tissues.

There are two known COX isoforms, COX-1 and COX-2, which, though physiologically distinct, are similar in amino acid sequence and enzymatic functions. COX-2 (EC 1.14.99.1) is not constitutively expressed and is generally undetectable in normal peripheral tissues (Kujubu et al., (1991) *J. Biol. Chem.* 266: 12866-12872; O'Banion et al. (1992) *Proc. Natl. Acad. Sci. U.S.A.* 89: 4888-4892). COX-2 expression is inducible (for example, by mitogens) and COX-2 mRNA levels rise rapidly in response to inflammatory stimuli such as interleukin-1β and lipopolysaccharide, and to decrease in response to glucocorticoids.

The term "COX-2-inhibitory compound" as used herein refers to an activity that inhibits any activity of COX-2 including a cycloxygenase (i.e., the prostaglandin-producing) activity, a binding activity of COX-2, or an ability of COX-2 to increase or decrease activation of the NMDA receptor. The difference in inhibition can be about 2-fold, about 5-fold, about 10-fold, about 100-fold, or about 1000-fold or greater. Inhibition of the cyclooxygenase enzyme is generally determined by measuring the $IC_{50}$, i.e., concentration of inhibitor that produces half-maximal inhibition of enzyme activity.

The term "detectable signal" as used herein refers to a signal in an amount sufficient to yield an acceptable image using equipment that is available for clinical, laboratory, or pre-clinical use. A detectable signal maybe generated by one or more administrations of the probes of the present disclosure. The amount administered can vary according to factors such as the degree of susceptibility of the individual, the age, sex, and weight of the individual, idiosyncratic responses of the individual, the dosimetry, and the like. The amount administered can also vary according to instrument and digital processing related factors.

The term "detection" of a signal as used herein refers typically to the use of a light detection device such as, but not limited to a charge-coupled detector that converts light energy to an electrical signal. It is known in the art that the light emissions from a source may be focused onto the detector for the formation of an image of the emitted light that may be observed visually by such as a physician.

The term "fluorescence" as used herein refers to a luminescence that is mostly found as an optical phenomenon in cold bodies, in which the molecular absorption of a photon triggers the emission of a photon with a longer (less energetic) wavelength. The energy difference between the absorbed and emitted photons ends up as molecular rotations, vibrations or heat. Sometimes the absorbed photon is in the ultraviolet range, and the emitted light is in the visible range, but this depends on the absorbance curve and Stokes shift of the particular fluorophore.

The term "fluorophore" as used herein refers to a component of a molecule or composition that causes a molecule to be fluorescent. It is a functional group in a molecule which will absorb energy of a specific wavelength and re-emit energy at a different (but equally specific) wavelength. The amount and wavelength of the emitted energy depend on both the fluorophore and the chemical environment of the fluorophore. Fluorescein isothiocyanate (FITC), a reactive derivative of fluorescein, has been one of the most common fluorophores chemically attached to other, non-fluorescent, molecules to create new fluorescent molecules for a variety of applications. Other historically common fluorophores are derivatives of rhodamine (TRITC), coumarin, and cyanine. Newer generations of fluorophores such as the ALEXA FLUORS™ and the DYLIGHT FLUORS™ are generally more photostable, brighter, and less pH-sensitive than other standard dyes of comparable excitation and emission.

The terms "fluorescence quencher" or "quencher" as used herein refers to molecules that interfere with or absorb the fluorescence emitted by a nearby fluorophore. Exemplary quenchers include, but are not limited to, Dabsyl or a BLACK HOLE QUENCHER® that are non-fluorescent aromatic molecules. A quencher can also be a second fluorescent molecule, for example TAMRA (carboxytetramethylrhodamine) that emits at a different wavelength.

The term "dye" as used herein refers to a fluorescent molecule, i.e., one that emits electromagnetic radiation, especially of visible light, when stimulated by the absorption of incident radiation. The term includes, but is not limited to, fluorescein, a xanthene dye having an absorption maximum at 495 nanometers. A related fluorophore is Oregon Green, a fluorinated derivative of fluorescein, indocyanine green (ICG) and the like. The term further includes bora-diaza-indecene, rhodamines, and cyanine dyes. A "rhodamine" is a class of dyes based on the rhodamine ring structure. Rhodamines include (among others): TETRAMETHYL-RHODAMINE®, and carboxytetramethyl-rhodamine (TAMRA).

Rhodamines are established as natural supplements to fluorescein based fluorophores, which offer longer wavelength emission maxima and thus open opportunities for multicolor labeling or staining. The term is further meant to include "sulfonated rhodamine," a series of fluorophores known as ALEXA FLUOR® dyes (Molecular Probes, Inc). These sulfonated rhodamine derivatives exhibit higher quantum yields for more intense fluorescence emission than spectrally similar probes, and have enhanced photostability, absorption spectra matched to common laser lines, pH insensitivity, and a high degree of water solubility. The term "dye" may also refer to any molecule known to quench fluorescence including QXL dyes, black holes quenchers and the like.

"Cyanines" are a family of cyanine dyes, Cy2, Cy3, Cy5, Cy7, and their derivatives, based on the partially saturated indole nitrogen heterocyclic nucleus with two aromatic units being connected via a polyalkene bridge of varying carbon number. These probes exhibit fluorescence excitation and emission profiles that are similar to many of the traditional dyes, such as fluorescein and tetramethylrhodamine, but with enhanced water solubility, photostability, and higher quantum yields. The excitation wavelengths of the Cy series of synthetic dyes are tuned specifically for use with common laser and arc-discharge sources, and the fluorescence emission can be detected with traditional filter combinations. The cyanine dyes generally have broader absorption spectral regions than members of the Alexa Fluor family.

The term "incident energy" as used herein refers to electromagnetic (optical) radiation between the wavelengths of about 350 nm to about 800 nm and which can be absorbed by the dyes or nanoparticles of the embodiments of the probes of the disclosure. The term "incident energy" may be construed to include laser light energy or non-laser energy.

The term "nanoparticle" refers to a material with dimensions below 1000 nm. These dimensions may be extended in any of three axes (x, y, z). Nanoparticles may be made naturally or synthetically. Nanoparticles may consist of multiple components including core, shell, and coat. The ratio of core, shell, and coat may differ with different batches of nanoparticles.

The term "derferoxamine" (also known as desferrioxamine B, desferoxamine B, DFO-B, DFOA, DFB or DESFERAL®) as used herein refers to a bacterial siderophore produced by the actinobacteria *Streptomyces pilosus* and having the chemical name N'-{5-[acetyl(hydroxy)amino]pentyl}-N-[5-({4-[(5-aminopentyl)(hydroxy)amino]-4-oxobutanoyl}amino)pentyl]-N-hydroxysuccinamide.

The term "GHK-Cu" as used herein refers to the copper peptide GHK-Cu, a naturally occurring copper complex of a glycyl-L-histidyl-L-lysine tripeptide. The GHK-Cu tripeptide has strong affinity for copper(II).

The term "subject" as used herein refers to a mammalian or non-mammalian non-human animal, or a human, subject or patient in receipt of a composition according to the present disclosure.

The terms "linker" and "cleavable linker" as used herein refer to any molecular structure that connects a fluorescence quencher entity to the fluorescent moiety of the disclosure. In particular, the linkers as used in the compositions of the disclosure should have at least one cleavable site that will, once cleaved, allow the quencher to be displaced from the vicinity of the fluorophore, thereby allowing emission of a detectable fluorescence signal. For example, a linker may be a peptide that can be cleaved by a peptidase or protease enzyme that can specifically bind to an amino acid motif within the linker. The linker may comprise a disulfide bond cleavable by a reduction reaction either enzymically catalyzed or due to the redox potential at the site of concentration of the activatable probe in a cell or tissue.

The term "peptide" as used herein refers to short polymers formed from the linking, in a defined order, of α-amino acids. The link between one amino acid residue and the next is known as an amide bond or a peptide bond. Proteins are polypeptide molecules (or consist of multiple polypeptide subunits). The distinction is that peptides are short and polypeptides/proteins are long. There are several different conventions to determine these. Peptide chains that are short enough to be made synthetically from the constituent amino acids are called peptides, rather than proteins, with one commonly understood dividing line at about 50 amino acids in length.

Modifications and changes can be made in the structure of the peptides of this disclosure and still result in a molecule having similar characteristics as the peptide (e.g., a conservative amino acid substitution). For example, certain amino acids can be substituted for other amino acids in a sequence without appreciable loss of activity. Because it is the interactive capacity and nature of a peptide that defines that peptide's biological functional activity, certain amino acid sequence substitutions can be made in a peptide sequence and nevertheless obtain a peptide with like properties.

In making such changes, the hydropathic index of amino acids can be considered. The importance of the hydropathic amino acid index in conferring interactive biologic function on a peptide is generally understood in the art. It is known that certain amino acids can be substituted for other amino acids having a similar hydropathic index or score and still result in a peptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant peptide, which in turn defines the interaction of the peptide with other molecules, such as enzymes, substrates, receptors, antibodies, antigens, and the like. It is known in the art that an amino acid can be substituted by another amino acid having a similar hydropathic index and still obtain a functionally equivalent peptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent peptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent peptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a peptide as set forth above. In particular, embodiments of the peptides can include variants having about 50%, 60%, 70%, 80%, 90%, and 95% sequence identity to the peptide of interest.

The term "liposome" as used herein refers to a spherical lipid and phospholipid particle in which individual lipid molecules cooperatively interact to create a bipolar lipid membrane that encloses and isolates a portion of the medium in which it was formed. A liposome may further encompass structures that envelop or encapsulate a probe according to the disclosure for delivery to a recipient human or non-human animal subject, whereupon the nanoprobe of the disclosure may be released from the liposome for binding to COX-2.

The term "pharmaceutically acceptable carrier" as used herein refers to a diluent, adjuvant, excipient, or vehicle with which a composition of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probes and pharmaceutically acceptable carriers preferably should be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

Pharmaceutical compositions and unit dosage forms of the disclosure typically also include one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that include primary or secondary amines are particularly susceptible to such accelerated decomposition.

The disclosure further encompasses pharmaceutical compositions and dosage forms that include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific example of a solubility modulator is tartaric acid.

Like the amounts and types of excipients, the amounts and specific type of active ingredient in a dosage form may differ depending on factors such as, but not limited to, the route by which it is to be administered to patients. However, typical dosage forms of the compounds of the disclosure include a pharmaceutically acceptable salt or salts, or a pharmaceutically acceptable polymorph, solvate, hydrate, dehydrate, co-crystal, anhydrous, or amorphous form thereof, in an amount of from about 10 mg to about 1000 mg, preferably in an amount of from about 25 mg to about 750 mg, more preferably in an amount of from 50 mg to 500 mg, even more preferably in an amount of from about 30 mg to about 100 mg.

Additionally, the compounds and/or compositions can be delivered using lipid- or polymer-based nanoparticles. For example, the nanoparticles can be designed to improve the pharmacological and therapeutic properties of drugs administered parenterally (Allen & Cullis (2004) *Science* 303: 1818-1822).

Topical dosage forms of the disclosure include, but are not limited to, creams, lotions, ointments, gels, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms including a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well known in the art. See, e.g., Remington's Pharmaceutical Sciences, 18th Ed., Mack Publishing, Easton, Pa. (1990).

Transdermal and mucosal dosage forms of the compositions of the disclosure include, but are not limited to, creams, lotions, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985).

Examples of transdermal dosage forms and methods of administration that can be used to administer the active ingredient(s) of the disclosure include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,446,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof, to form dosage forms that are nontoxic and pharmaceutically acceptable.

Penetration enhancers can be used to assist in delivering the active ingredients to or across the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of a tight junction modulator can be used to further adjust the properties of the resulting composition.

The term "physiologically acceptable" as used herein refers to a composition that, in contact with a cell, isolated from a natural source or in culture, or a tissue of a host, has no toxic effect on the cell or tissue or substantially diminishes the viability or physiology of the recipient cell.

The term "cancer:" as used herein shall be given its ordinary meaning and is a general term for diseases in which abnormal cells divide without control. Cancer cells can invade nearby tissues and can spread through the bloodstream and lymphatic system to other parts of the body.

There are several main types of cancer, for example, carcinoma is a cancer that begins in the skin or in tissues that line or cover internal organs. Sarcoma is a cancer that begins in the bone, cartilage, fat, muscle, blood vessels, or other connective or supportive tissue. Leukemia is cancer that starts in blood-forming tissue such as bone marrow, and causes large numbers of abnormal blood cells to be produced and enter the bloodstream. Lymphoma is cancer that begins in the cells of the immune system. The probes and methods of the disclosure are especially advantageous for detecting cancer cells and tumors localized to a specific site in an animal or human, although it is contemplated that the systems may be useful to detect circulating cells and in particular a cancerous epithelial or skin lesion.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it with differing processes that have gone awry. Solid tumors may be benign (not cancerous), or malignant (cancerous). Different types of solid tumors are named for the type of cells that form them.

Description

The present disclosure encompasses pharmaceutically acceptable compositions formulated for the topical or transdermal delivery of probes specific for cyclooxygenase-2 (COX-2) of human and non-human subjects. In particular, the disclosure provides compositions that comprise an activatable probe comprising a fluorescent moiety comprising a fluorophore attached to a compound having selective affinity for COX-2, and further includes a removable fluorescence quencher linked to the fluorescent moiety by a cleavable linker.

Upon delivery to a recipient human or non-human animal subject, the activatable probe can contact a cell, population of cells, or a tissue that has a greater concentration of the COX-2 enzyme than do other cells or tissues in the recipient subject. Accordingly, the activatable probe compound that has affinity for COX-2 will selectively bind to the COX-2, thereby localizing and concentrating the probe. It is anticipated that cells or tissues that have these elevated levels of COX-2 will also include an enzyme, have a pH level, or a redox potential that is capable of cleaving the linker and so releasing the fluorescence quencher from the vicinity of the bound and localized fluorescent moiety. Subsequent irradiation by an activating incident illumination with result in a fluorescent emission signal that can be detected, most advantageously by a signal sensitive detector capable of generating an image that can be visualized by an observer.

It has been found that the inclusion of the removable fluorescent quencher combined with the selectivity of the fluorescent moiety for the COX-2 not only provides a localization of the probe to a target such as a tumor or other cell or tissue having elevated and/or pathological levels of COX-2 activity but provides a significant and unexpected lowering of background fluorescence levels. The differential between the background fluorescence level and that generated by a COX-2-enhanced site substantially increases the sensitivity of detection of small, highly localized concentrations of the probe in such as a small (<1 mm) tumor cell mass. Accordingly, the activatable probes of the disclosure offer enhanced sensitivity for imaging such as a cancer tumor and earlier detection than would otherwise be possible with current non-quenchable probes.

In some embodiments of the activatable probes of the disclosure, but not intended to be limiting, reduced levels of non-specific background fluorescence can result from the application of probes comprising Fluorocoxib A (LM-477) and derivatives thereof to a tissue, an epithelial surface, or the dermal surface of an animal or human subject.

Fluorocoxib A has specificity for cyclooxygenase-2 (COX-2) due to specific binding to the enzyme and, therefore, tends to concentrate in cells that have accumulated this enzyme. Typically due to abnormal up-regulation of expression, there is also generated a detectable level of non-specific accumulation of the fluorescent signal, particularly when the probe is delivered topically.

When the probe is administered systemically, despite of the wide distribution of the probe throughout all the body, it has been found that the probes according to the disclosure can concentrate in COX-2-over-expressing tissues, reaching maximum signal-to-noise and tumor-to-background (TBR) ratios between 3-7 h after fluorocoxib administration. However, for skin or other epithelial applications, as well as to improve on its TBR on systemic administration, it is desirable to limit the non-specific signal. To overcome this undesirable background fluorescent signal that can mask signals from smaller tumors and other sites having low-level expression of COX-2, the present disclosure provides molecular probes wherein the fluorescent COX-2-specific construct comprises a fluorescent quencher linked to the probe by a cleavable linker. Upon entry into a cell and binding of the Fluorocoxib to COX-2, the quencher can be displaced from the vicinity of the fluorophore by, for example, a cytoplasmic peptidase cleavage of the cleavable linker, allowing the generation of a detectable fluorescent signal. Consequently, there is a substantially reduced non-specific background signal in the absence of cellular uptake or COX-2 activity. While a most advantageous compound having selective affinity for COX-2 is Fluorocoxib (including but not intended to be limiting, other compounds, including COX-2 inhibitors such as CELOCOXIB®, PARECOXIB®, VADECOXIB®, ETORICOXIB®, LUMIRACOXIB®, and the like may be usefully employed in the activatable probes of the disclosure.

It is contemplated that the compositions of the disclosure can comprise any moiety that can specifically bind to COX-2 and to which a fluorophore can be linked. Any fluorescent molecule may be incorporated into these constructs with the proviso that there is also available a suitable corresponding quenching agent that may also be incorporated into the probe. Most advantageously, the quenching agent is linked to the fluorophore-COX-2 ligand combination by a linker that is cleavable either by a physiologic change, including changes in pH or redox state, or by an enzyme specific to a target site in the linker.

In some embodiments of the disclosure, the fluorescent moiety itself is autoquenching. High concentrations of most fluorophores are not fluorescent because they autoquench. For example, ICG (Indocyanine Green, sodium 4-[2-[(1E,3E,5E,7Z)-7-[1,1-dimethyl-3-(4-sulfonatobutyl)benzo[e]indol-2-ylidene]hepta-1,3,5-trienyl]-1,1-dimethylbenzo[e]indol-3-ium-3-yl]butane-1-sulfonate) is dark until diluted (most of the Weissleder probes are based on this phenomena where large complexes with multiple fluorophores are bound and then when cleaved off of the complex begin to fluoresce as they diffuse away from each other).

It is contemplated, therefore, that complexes of multiple Cox-2 probe entities that are dark in preparations prior to administration to a subject may be injected intravenously and then as they enter the tumor microenvironment are cleaved into monomers that fluoresce, enter cells, bind to Cox-2, and so retaining the fluorophore in the tumor cell. This process can confer a bi-partite specificity on the probes of the disclosure: one being a tumor-specific protease, and the other a Cox-2 specificity. This double-specificity can serve to reduce the detectable signal at non-malignant sites of inflammation where the tumor-specific proteases are absent.

The fluorophore-COX-2-specific activatable probes of the disclosure can be formulated into pharmaceutically acceptable compositions for topical administration to tissue surfaces, including the dermal surface, of a subject for the detection of cancerous lesions of these organs including the skin. It has been found that this route of delivery of the molecular probe results in substantially reduced systemic delivery, significantly contributing to reducing the accumulation of non-specific background fluorescence. This facilitates the detection of small lesions either at an early stage, after treatment, or with otherwise weaker signals by increasing the differential between a detectable signal from a lesion and the background signal. This increases the ability of a physician to apply therapeutic protocols to reduce or eliminate the development of a cancer with a high probability of morbidity at an earlier stage of the tumor development than would otherwise be possible. For example, but not intended to be limiting, if a melanoma is detected before it reaches a diameter of 1 mm and treated, survival rate for the patient can increase by at least 50%.

It is contemplated that the pharmaceutically acceptable compositions of the disclosure, while useful in dermal applications, may also be formulated for delivery to epithelial surfaces such as the lining of the stomach, colon and esophagus. In these applications the composition and the formulations can be the same as for application to the skin, or may be formulated for application to a specific tissue or organ. For example, lecithin liposomes encapsulating the activatable probes of the disclosure may be coated with compounds such as sulfasalazine. When cleaved by colonic bacteria the liposomes are disrupted and release for absorption by the epithelial layer.

It is further contemplated that the COX-2-specific probes of the disclosure may be formulated in a pharmaceutically acceptable composition for administering systemically to a human or non-human animal subject, thereby providing a reduced non-specific background detectable signal, and hence improving the detection of cancerous cells and tissues or cells or inflamed tissues producing and accumulating elevated levels of COX-2.

Fluorocoxib for use in the compositions of the disclosure was synthesized by labeling indomethacin with 5-Rox-D through an amide linkage, which confers specificity for COX-2 relative to COX-1 (Uddin M J et al., (2010) *Cancer Res.* 70: 3618-3627). The capability of this probe to detect early stage skin tumors that cannot be detected by visual inspection was investigated. Spontaneous mouse models of basal cell carcinoma (BCC) and squamous cell carcinoma (SCC) were used as well as allograft and xenograft models of BCC and melanoma.

Figure 1B:
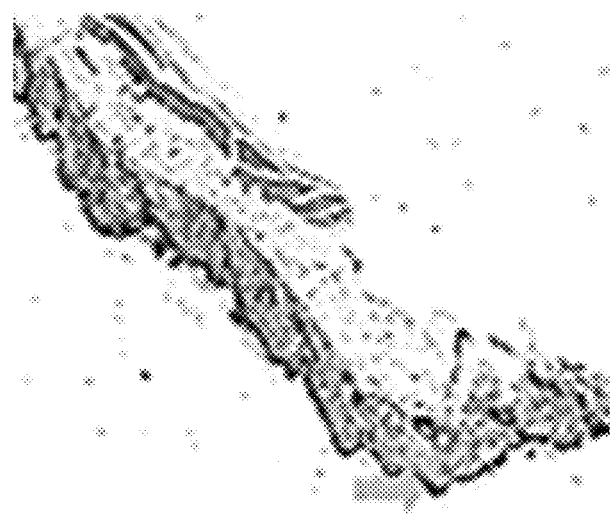

Three hours after retro-orbital injection of Fluorocoxib probe, in vivo imaging and tissue histology demonstrated that fluorescence was selectively detected in areas with visible multiple macroscopic tumor masses, as well as microscopic tumors sized from about 100 to about 150 µm, as shown in FIG. 1, arrowed. This indicates the potential for early detection of BCC, SCC and melanoma by in vivo imaging of Fluorocoxib A. Fluorocoxib A was undetectable in mouse blood after topical application by LC/MS-MS quantification.

Figure 2:
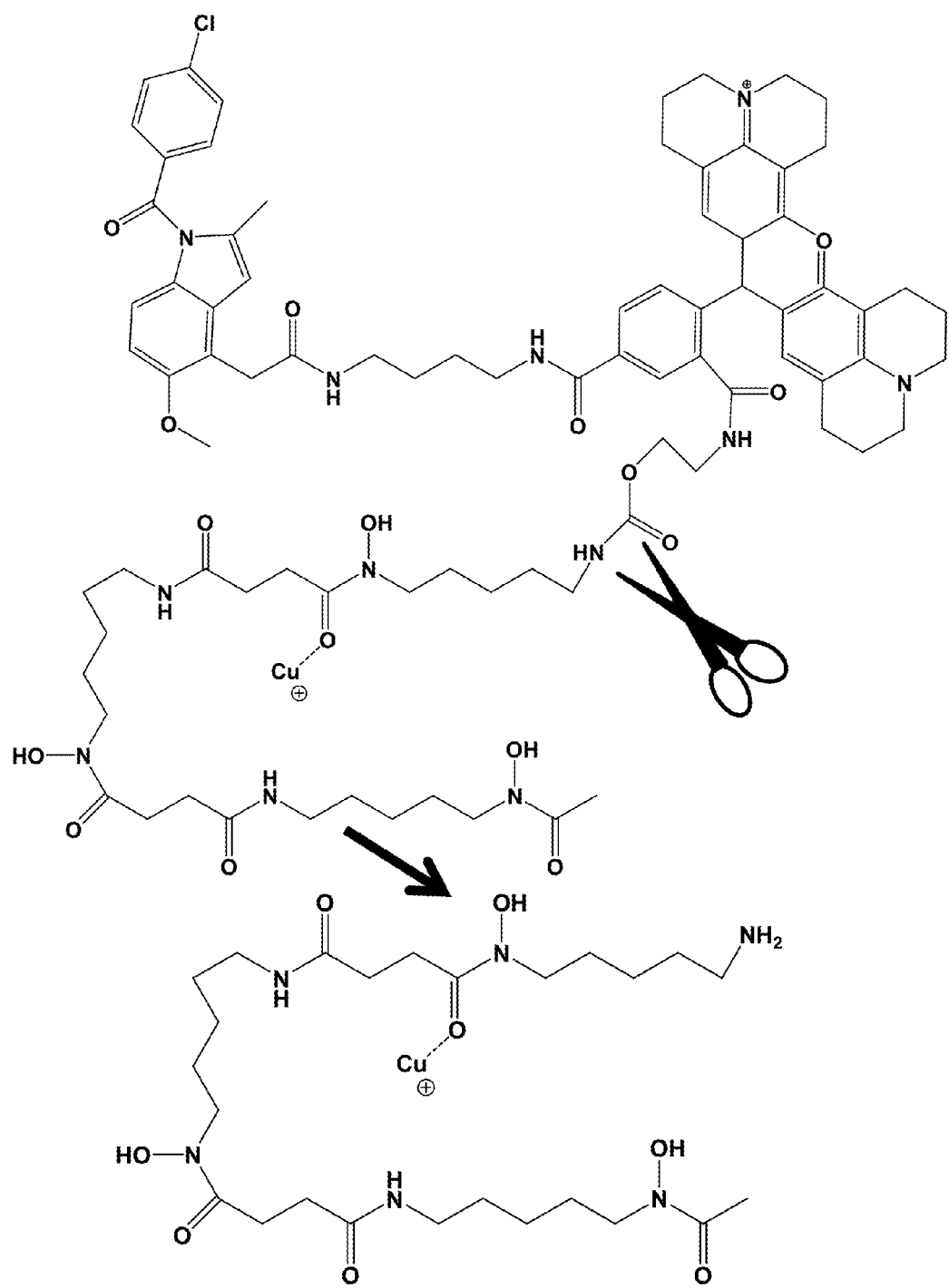
FIG. 2 illustrates the mechanism of Fluorocoxib fluorescence activation where GHK-Cu ((a naturally occurring tripeptide) is a quencher linked to Fluorocoxib through an aminoethanol linker that can be cleaved intracellularly by carboxylesterases. Fluorocoxib-linked DFO /copper forms a less fluorescent molecule. In the proximity of cancer cells, DFO is cleaved by esterases, thereby allowing unquenched fluorescence.
Figure 5:
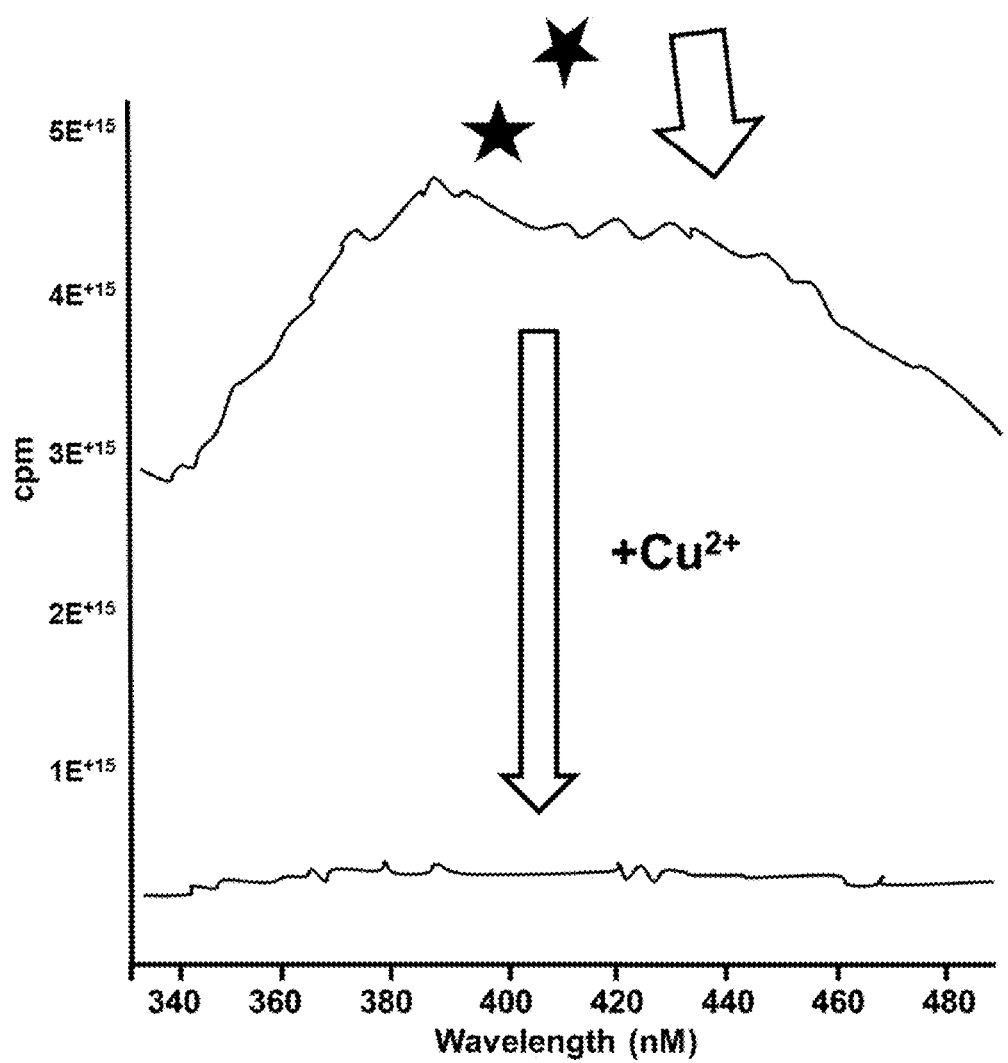
FIG. 5 illustrates the quenching by Cu$^{2+}$ ions of fluorescence from Fluorocoxib-GHK.
Figure 6:
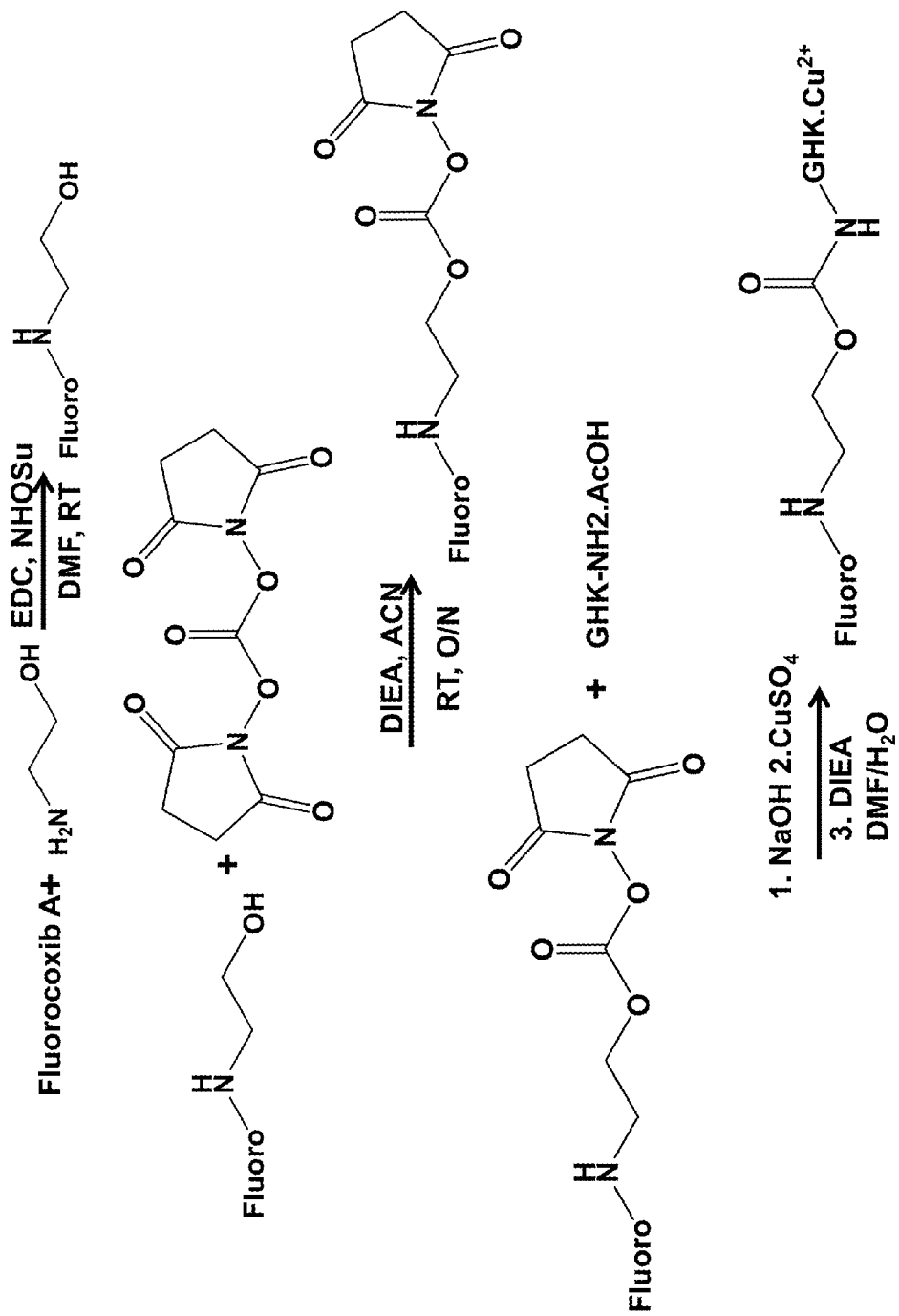
FIG. 6 illustrates a schema for the synthesis of Fluorocoxib-GHK.Cu$^{2+}$.

To decrease non-specific fluorescence according to the disclosure, Fluorocoxib can be first absorbed in a resin. Most advantageously, however, in some embodiments of the disclosure, a fluorescent moiety as exemplified by such as Fluorocoxib A, may be conjugated to a cleavable linker such as GHK-Cu, an FDA-approved highly cationic copper-containing compound, thereby forming an activatable probe Fluorocoxib-GHK-Cu complex that results in quenched fluorescence. Fluorocoxib-GHK fluorescence can be quenched by adding copper ions such that, before cleavage of the quencher from the complex fluorescence reduction can be reduced by as much as 20-fold at some wavelengths (as shown in FIG. 5, for example). When the Fluorocoxib-GHK-Cu is taken into the cell, or when it binds to its specific COX-2 target, the quencher is released from the probe, as shown, for example, in FIG. 5. This will result in the release of the GHK-Cu (as schematically shown in FIG. 2). A procedure for the synthesis of Fluorocoxib linked to the copper peptide GHK-Cu is shown in FIG. 6.

It is contemplated that a variety of quenchers may be incorporated into the compositions of the present disclosure, selected for their ability to quench fluorescence from a variety of fluorescent compounds, and linkers will be used in combination with indomethacin, its derivatives and other COX-2 inhibitors, to achieve early diagnosis of cancers of the skin and other organs. Suitable quenchers include, but are not limited to, DFO, IRDyeO QC-1 (capable of quenching a broad spectrum of dyes including Fluorescein (emission maximum 540 nm), Cy3 (570 nm), Cy5 (670 nm), IRDye 680 (700 nm), IRDye 700DX (690 nm), or IRDye 800CW (790 nm), and photon-induced fluorescence transfer (PeT)-based quenchers, alone or in combination with H-dimer forming xanthenes containing fluorophores.

In the compositions of the disclosure, it is contemplated that the fluorescence quencher can be attached to the Fluorocoxib-GHK-Cu by a cleavable linker such as, but not limited to, a GDEVDGAK peptide (cleavable by caspase 3), disulfide-based linkers, acid-cleavable hydrazone linkers, linkers cleavable by tumor-specific lysosomal proteases (cathepsin, plasmin, and the like) and esterases, and the like.

Figure 3:
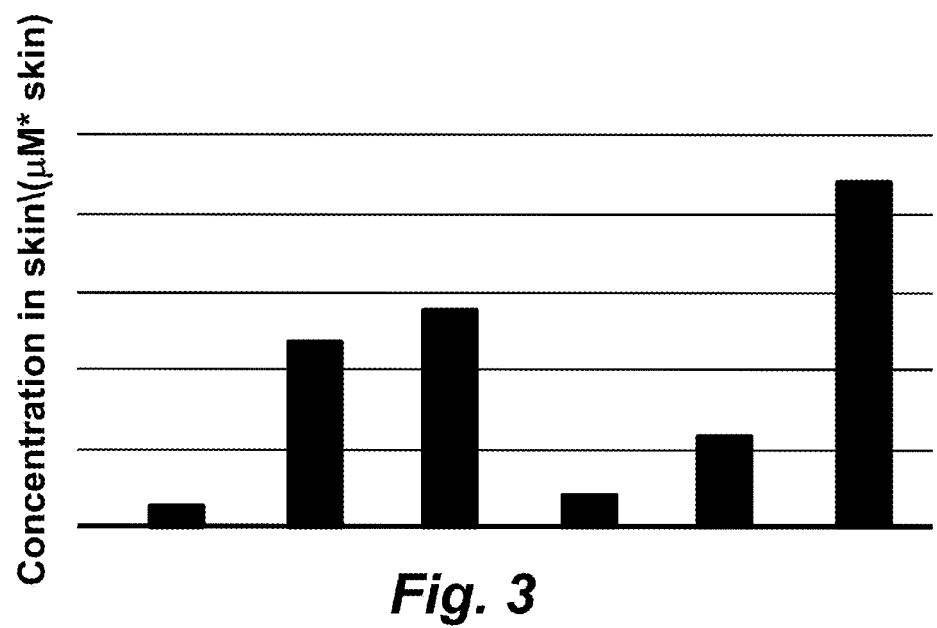
FIG. 3 illustrates Liquid Chromatography/Mass Spectrometry (LC/MS-MS) quantification of Fluorocoxib accumulation in vivo in mouse tumors after topical application.
Figure 4:
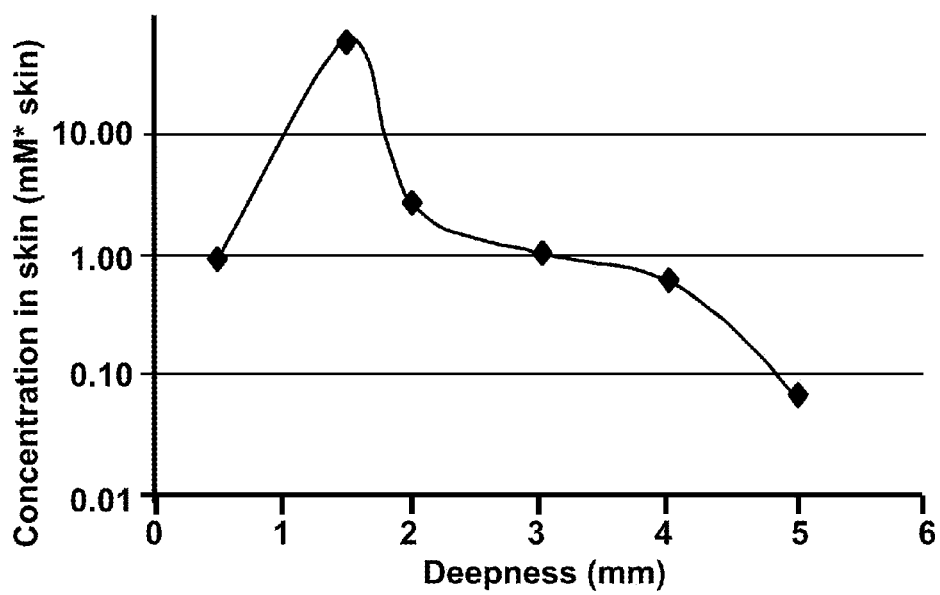
FIG. 4 illustrates a Fluorocoxib-based topical formulation according to the disclosure applied to human BCC biopsies obtained from human excised tumors. The tissue was sectioned from the top (0.5 mm thick sections) to the bottom 3 hours after application and tissue slices were analyzed by LC/MS-MS for Fluorocoxib accumulation per tissue in depth.

To make the Fluorocoxib a useful diagnostic agent in human for non-melanoma skin cancer (NMSC), it is advantageous to formulate it into a topical cream such as a 1% Fluorocoxib cream in a formula comprising PBS and propylene glycol. There was good absorption of such a composition on mouse (FIG. 3) and human skin (FIG. 4).

In embodiments of the disclosure, the activatable probes of the disclosure such as Fluorocoxib-GHK-Cu, may be incorporated into liposomes such as, but not limited to, chitosanized egg lecithin, to form liposomes with a negatively charged surface. The negative charge will be neutralized by adding the biocompatible chitosan. Such liposomes can be further formulated in a topical formulation to increase skin penetration to be used for early detection of NMSC, melanoma and other skin or epithelial cancers.

It has been shown that chitosan nanoparticles can penetrate through the keratinized layers of the epidermis thus significantly enhancing intradermal drug delivery. Penetration of Fluorocoxib formulations through the skin layers has now been shown (FIGS. 3 and 4).

One aspect of the disclosure, therefore, encompasses embodiments of a composition comprising an activatable probe for the detection of a cell or tissue having cyclooxygenase-2 (COX-2) activity, said activatable probe comprising: (i) a fluorescent moiety comprising a compound capable of selectively binding to COX-2 and a first fluorophore attached thereto; and (ii) a fluorescence quencher selected to quench a fluorescent emission from said fluorophore, wherein the fluorescent moiety and the fluorescence quencher are connected by a cleavable linker.

In embodiments of this aspect of the disclosure, the compound capable of selectively binding to COX-2 can be a COX-2 inhibitor.

In embodiments of this aspect of the disclosure, the COX-2 inhibitor can be indomethacin, celecoxib, or a derivative thereof.

In embodiments of this aspect of the disclosure, the fluorescent moiety can be a Fluorocoxib.

In embodiments of this aspect of the disclosure, the fluorescent quencher can be selected from the group consisting of: a peptide, a peptide in association with a metal ion, deferoxamine, D-penicillamine, dimercaptosuccinic acid, and 2,3-dimercapt-propane-sulfonate.

In embodiments of this aspect of the disclosure, the fluorescent quencher can be a second fluorophore that quenches an emission from the first fluorophore when attached to the fluorescent moiety.

In embodiments of this aspect of the disclosure, the cleavable linker can be cleavable by an enzyme, by a change in pH, or by the redox potential of a tumor or cancerous cell.

In embodiments of this aspect of the disclosure, the cleavable linker comprises a cleavable disulfide bond or a peptide bond.

In some embodiments of this aspect of the disclosure, the activatable probe is encapsulated in a liposome. In these embodiments of this aspect of the disclosure, the liposome can further comprise a biocompatible compound for selectively delivering the liposome to an epithelial cell of the intestinal tract of a human or non-human animal subject.

In embodiments of this aspect of the disclosure, the biocompatible compound can be selected from the group consisting of: sulfasalazine, balsalazide, and olsalazine.

In embodiments of this aspect of the disclosure, the activatable probe can consist essentially of Fluorocoxib A conjugated to GHK-$Cu^+$ or Fluorocoxib A conjugated to DFO-$Cu^+$.

In embodiments of this aspect of the disclosure, the composition can further comprise a pharmaceutically acceptable carrier.

Another aspect of the disclosure encompasses embodiments of a method of detecting a COX-2 activity in a human or non-human animal tissue or cell thereof, the method comprising the steps of: (a) administering to a recipient human or non-human animal subject a pharmaceutically acceptable composition comprising an activatable probe comprising: a fluorescent moiety comprising a compound capable of selectively binding to COX-2 and a fluorophore attached thereto; a fluorescence quencher selected to quench a fluorescent emission from said fluorophore, wherein the fluorescent moiety and the fluorescence quencher are connected by a cleavable linker; and a pharmaceutically acceptable carrier, wherein the pharmaceutically acceptable composition can be delivered to the recipient subject by a route that delivers the activatable probe to a tissue suspected of having COX-2 activity; (b) irradiating the recipient tissue or isolated cell with a stimulatory incident energy, whereupon the fluorophore can emit a detectable signal if the fluorescence quencher has been cleaved from the fluorescent molecular probe; and (c) detecting the emitted detectable signal, thereby detecting the presence of COX-2 in the recipient tissue or cell.

In embodiments of this aspect of the disclosure, the pharmaceutically acceptable composition can be formulated for transdermal delivery to the skin or an epithelial surface of the recipient subject, and wherein in step (a) said composition can be administered topically to the skin or an epithelial surface of the recipient subject.

In embodiments of this aspect of the disclosure, the method can further comprise the steps of: (i) obtaining an image of the detectable signal; and (ii) overlaying the image from step (i) onto an image of the recipient human or non-human animal subject, thereby determining the location of COX-2 in a tissue of said subject.

In embodiments of this aspect of the disclosure, the activatable probe can comprise Fluorocoxib A conjugated to GHK-$Cu^+$ or Fluorocoxib A conjugated to DFO-$Cu^+$.

In embodiments of this aspect of the disclosure, the probe can be encapsulated in a liposome.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Fluorocoxib-GHK Preparation: As shown in FIG. 6, Fluorocoxib A (Uddin M J et al., (2010) *Cancer Res.* 70: 3618-3627) (7 mg), ethanolamine (2.3 mg) and N-hydroxysuccinimide (NHS) (1.3 mg) in dimethyl formamide (DMF, 1 ml) were mixed and stirred at room temperature, and then ethylene dichloride (EDC) (1.5 mg) added to this solution. This mixture was stirred overnight.

After evaporating the DFM, the residue was treated with 20 ml ethyl acetate and then washed twice with brine. The organic phase was dried by using anhydrous sodium sulfate. Ethyl acetate was removed by evaporated under reduce pressure. The crude solid was used without purification for the next step.

The product from above reaction was treated with N,N-disuccinimidyl carbonate (13.6 mg in acetonitrile (CAN) (3 ml)) and N,N-diisopropylethylamine (DIEA) (21 μl) and stirring at room temperature overnight. All solvents were then removed by reduce pressure.

The residue was dissolved in minimum amount of DMF and to this 18.1 mg of GHK, one equivalent of copper sulfate and 0.5 ml water were added. This solution was adjusted to pH 6.5 using sodium hydroxide (as shown in Scheme 2, FIG. 6). The mixture was stirred at room temperature overnight. All solvents were removed by reduce pressure and the crude of final compound was further purified using HPLC.

Example 2

Figure 7:
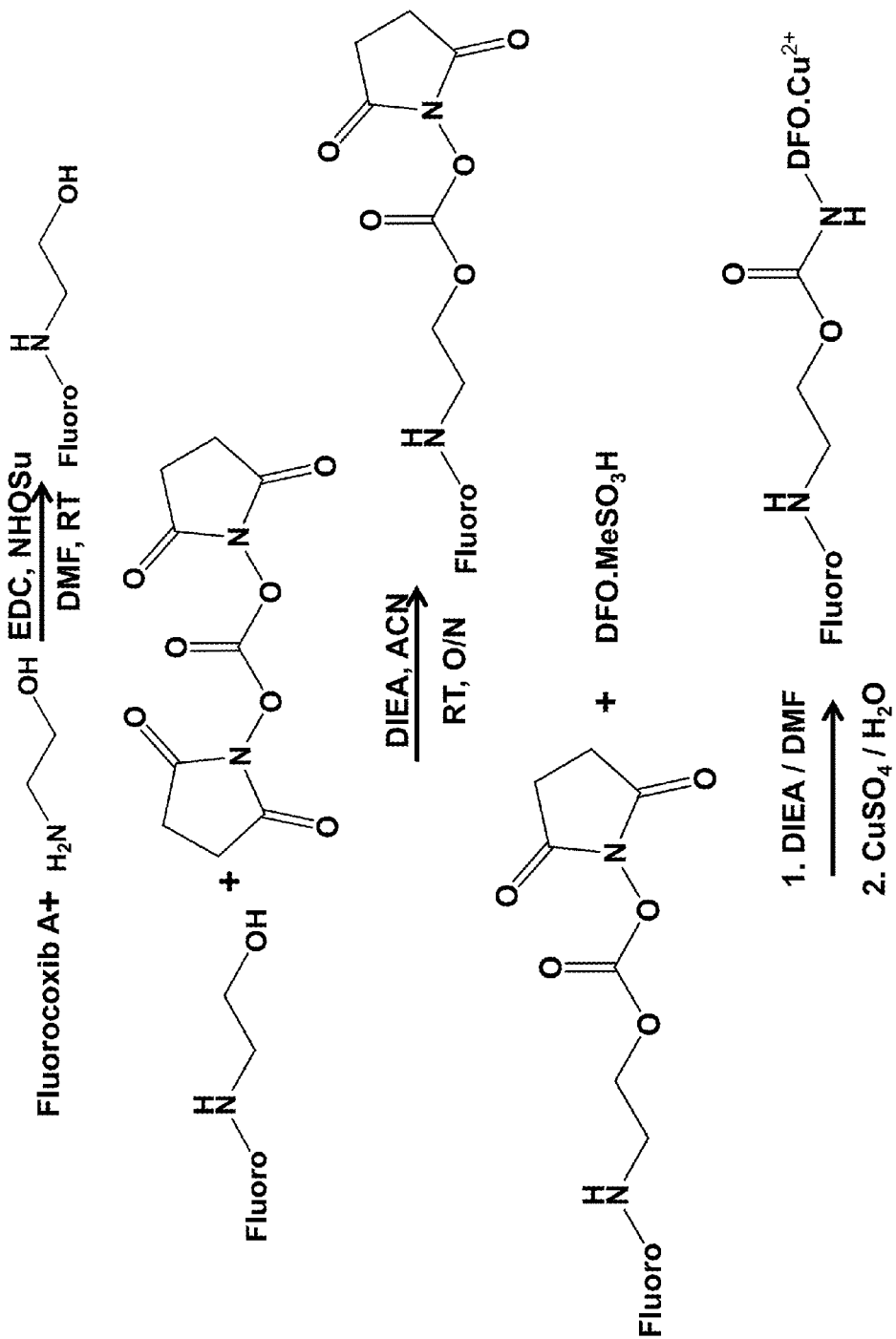
FIG. 7 illustrates a schema for the synthesis of Fluorocoxib-DFO.Cu$^{2+}$.

Fluorocoxib-DFO Preparation: As shown in FIG. 7, Fluorocoxib A (7 mg), ethanolamine (2.3 mg) and N-Hydroxysuccinimide (NHS) (1.3 mg) in dimethyl formamide (DMF, 1 ml) were stirred at room temperature, and then EDC (1.5 mg) added to this solution. This mixture was stirred overnight.

After evaporating the DFM, the residue was treated with 20 ml ethyl acetate (EtOAc) and then washed twice with brine. The organic phase was dried by using anhydrous sodium sulfate. EtOAc was removed by evaporated under reduce pressure. The crude solid was used without purification for the next step.

The product from above reaction was treated with N,N-disuccinimidyl carbonate. The crude product was dissolved in 1 ml DMF, then combined with DFO.$MeSO_3H$ (34.9 mg) and DIEA (18.5 μl). The mixture was stirred at room temperature overnight. 0.1 ml solution of $CuSO_4$ (1 mg/ml) was then added into mixture which was then stirred for 30 min. All solvents were removed by reduce pressure and the final compound was purified using HPLC.

Example 3

Fluorocoxib Preparation (II): As shown in FIG. 7, 100 mg of Fluorocoxib, 38 mg of methyl ester lysine with one equivalent of EDC, sulfo-NHS were dissolved in 3 mL of DMF stirred for 18 h at room temperature periodically checking the progress of reaction using thin-layer chromatography.

After completion of the reaction, the DMF was removed by rotary evaporation. The residue was dissolved in ethyl acetate and washed by: sodium bicarbonate, sodium chloride. The organic phase was dried with anhydrous sodium sulfate. After removing all solvents, the residue was purified by preparative thin-layer chromatography. 70 mg compound (I) (yield 50%) was obtained.

As shown in FIG. 6, compound (I) was dissolved in mix solvents DCM/DMF (3 ml/2 ml) and cooled to 0° C. TFA was then added drop wise at 0° C. The reaction mixture was stirred at 0° C. for 1 h, and then slowly warmed to room temperature with continuous stirring, followed by TLC. After completed of reaction, all solvents were removed by reduced pressure keeping the temperature lower than 35° C.

Figure 8:
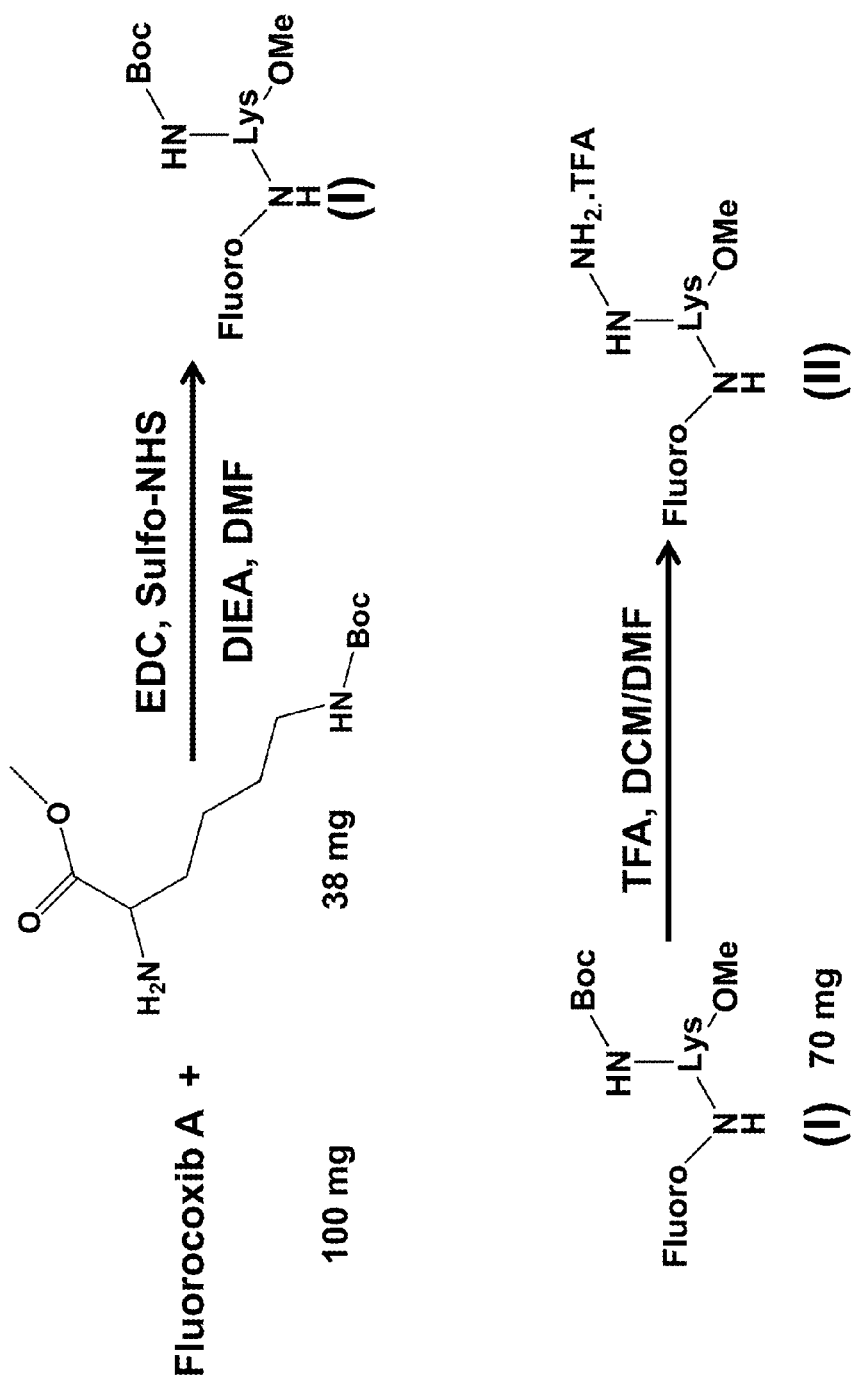
FIG. 8 illustrates a schema for the synthesis of Fluorocoxib-DFO.Cu$^{2+}$ where the DFO is linked to the Fluorocoxib by a cleavable disulfide bridge.
Figure 8:
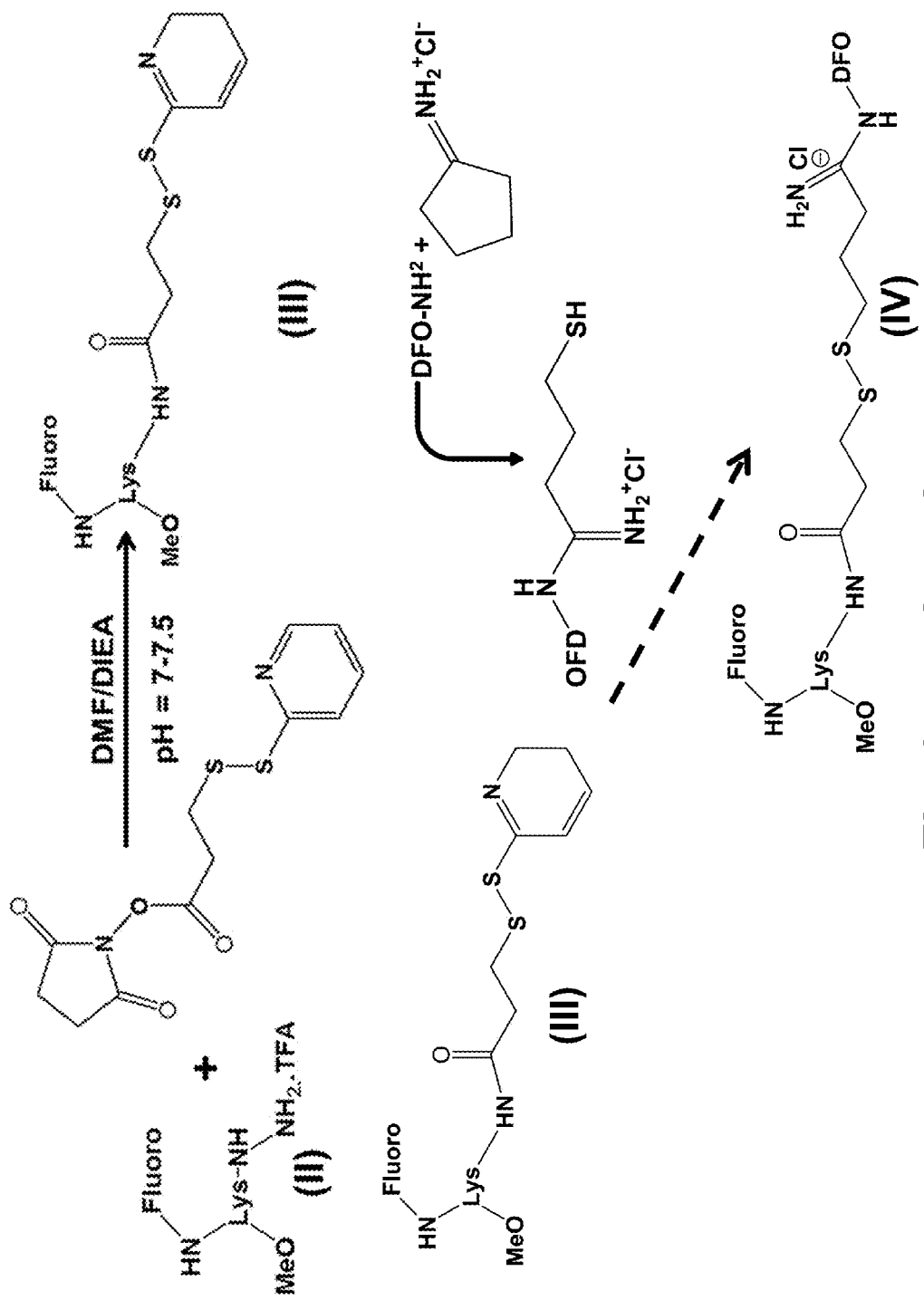

As shown in FIG. 8, compound (II) was dissolved in 2 mL DMF and adjusted to pH 7-7.5 by DIEA. Succinimidyl 3-(2-pyridyldithio)propionate (SPDP) reagent was added with constant stirring for 30 min at room temperature.

Example 4

Fluorocoxib cream was applied to human tumor sample overnight. After tissue was cleaned, it was sectioned into 1 mm slices (100 μM×10) and weighed.

3/1 w/v LIBERASE TL®, 0.5 mg/ml (Roche Bioscience) was added to ensure that the tissue was covered with enzyme in 1.5 ml Eppendorf centrifuge tube. Incubation was for 1 h at 37° C. with shaking. To ensure the sample was homogeneous, it was sonicated with probe. Preparation of Skin Samples for MSMS Analysis: Samples were defrosted at room temperature. Tumor slices were placed on glass slide, 10 slides/mm. Ten (10) slides (or what was available were scrapped to a pre-weighed Eppendorf centrifuge tube, and the tissue weighed. 3:1, v/w LIBERASE TL® 0.5 mg/ml (Roche Bioscience) was added (about 500 μl to every 150 mg of tissue)

and incubated at about 37° C. for 30 min (or until homogeneous), with periodic vortexing, and finally sonication. Samples were analyzed using the MS system: Sciex 4000, Mass/Setting, Q1/Q3/DP/CE/CXP.+

HPLC Conditions: Shimadzu LC208B, binary pump; Mobile Phase(s): A: 0.5 mM HFBA with 0.1% FA; B: Acetonitrile with 0.1% FA; Analytical Column: Ascentics CN, 5 µM, 50×2.1 mm; Column Temperature: Ambient; Injection volume: 10 µL; Total Flow, ml/min: 0.5.

The concentration of Fluorocoxib in tumor slices is shown in FIG. 4.

We claim:

1. A composition comprising an activatable probe for the detection of a cell or tissue having cyclooxygenase-2 (COX-2) activity, said activatable probe comprising:
   (i) a fluorescent moiety consisting of indomethacin conjugated to 5-Rox-D (Fluorocoxib); and
   (ii) a fluorescence quencher, wherein the fluorescent quencher is GHK-$Cu^+$, wherein the fluorescent moiety and the fluorescence quencher are connected by a cleavable linker comprising a cleavable peptide bond, wherein the linker is GHK, wherein the activatable probe is encapsulated in a liposome comprising sulfasalazine.

2. The composition of claim 1, further comprising a pharmaceutically acceptable carrier.

3. A method of detecting a COX-2 activity in a human or non-human animal tissue or cell thereof, the method comprising the steps of:
   (a) administering to a recipient human or non-human animal subject a pharmaceutically acceptable composition comprising an activatable probe for the detection of a cell or tissue having cyclooxygenase-2 (COX-2) activity, said activatable probe comprising:
      (i) a fluorescent moiety consisting of indomethacin coniuqated to 5-Rox-D (Fluorocoxib).
      (ii) a fluorescence quencher, wherein the fluorescent quencher is GHK-$Cu^+$, wherein the fluorescent moiety and the fluorescence quencher are connected by a cleavable linker comprising a cleavable peptide bond, wherein the linker is GHK, wherein the activatable probe is encapsulated in a liposome comprising sulfasalazine; and
      (iii) a pharmaceutically acceptable carrier,
   wherein the pharmaceutically acceptable composition is delivered to the recipient subject by a route that delivers the activatable probe to a tissue suspected of having COX-2activity;
   (b) irradiating the recipient tissue or isolated cell with a stimulatory incident energy, whereupon the fluorophore emits a detectable signal if the fluorescence quencher has been cleaved from the fluorescent molecular probe; and
   (c) detecting the emitted detectable signal, thereby detecting the presence of COX-2 in the recipient tissue or cell.

4. The method of claim 3, wherein the pharmaceutically acceptable composition is formulated for transdermal delivery to the skin or an epithelial surface of the recipient subject, and wherein in step (a), said composition is administered topically to the skin or an epithelial surface of the recipient subject.

5. The method of claim 3, further comprising the steps of:
   (i) obtaining an image of the detectable signal; and
   (ii) overlaying the image from step (i) onto an image of the recipient human or non-human animal subject, thereby determining the location of COX-2 in a tissue of said subject.

6. The method of claim 4, further comprising the steps of:
   (i) obtaining an image of the detectable signal; and
   (ii) overlaying the image from step (i) onto an image of the recipient human or non-human animal tissue, or cell isolated therefrom, thereby determining the location of COX-2 in the recipient tissue or cells.

* * * * *